United States Patent [19]

Coombs et al.

[11] 3,997,574
[45] Dec. 14, 1976

[54] 9-α-METHYL-STEROIDS

[75] Inventors: Robert V. Coombs, Chatham, N.J.; Eugene E. Galantay, Liestal, Switzerland

[73] Assignee: Sandoz, Inc., E. Hanover, N.J.

[22] Filed: Sept. 5, 1974

[21] Appl. No.: 503,276

Related U.S. Application Data

[63] Continuation of Ser. No. 358,379, May 8, 1973, abandoned, which is a continuation-in-part of Ser. No. 237,498, March 23, 1972, abandoned, which is a continuation-in-part of Ser. No. 109,612, Jan. 25, 1971, abandoned.

[52] U.S. Cl. .................. 260/397.45; 260/397.5; 260/239.55 C; 424/243

[51] Int. Cl.² .................................. C07J 5/00

[58] Field of Search ............ 260/397.45, 239.55 C, 260/397.5

[56] References Cited

UNITED STATES PATENTS 3,798,215   3/1974   Galantay et al. ......... 260/239.55 C Primary Examiner—Elbert L. Roberts
Attorney, Agent, or Firm—Gerald D. Sharkin; Richard E. Vila; Frederick H. Weinfeldt

[57] ABSTRACT

The compounds are 13-(lower)alkyl-9α-methyl-17α-propadienylgona-4-en-17β-ol-3-ones and derivatives thereof, e.g. 9α-methyl-17α-propadienylestra-17β-ol-3-one, and are useful as progestational agents.

15 Claims, No Drawings

9-α-METHYL-STEROIDS

This is a continuation of then copending application Ser. No. 358,379, filed May 8, 1973 (now abandoned), which, in turn, is a continuation-in-part of then copending application Ser. No. 237,498, filed March 23, 1972 (now abandoned), which, in turn, is a continuation-in-part of then copending application Ser. No. 109,612, filed Jan. 25, 1971 (now abandoned).

This invention relates to steroidal compounds, and more particularly to 13-alkyl-9α-methyl-17α-propadienylgona-4-en-17β-ol-3-ones, to the preparation of such compounds and to intermediates in the preparation of such compounds, as well as to compositions containing such compounds and to the use of such compositions.

The compound of the invention may be conveniently represented by the structural Formula I:

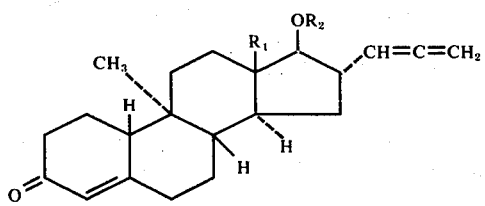

I wherein
 $R^1$ is alkyl having from 1 to 3 carbon atoms, i.e. methy, ethyl, n-propyl and isopropyl, and is preferably unbranched; and
 $R^2$ is a hydrogen atom, methyl, acetoacetyl or alkanoyl having from 2 to 4 carbon atoms, e.g. acetyl, propionyl and butyryl, including isomeric forms where they exist, and is preferably unbranched alkanoyl.

The compounds of the formula I may be obtained by Process 1 involving subjecting a corresponding compound of the Formual II:

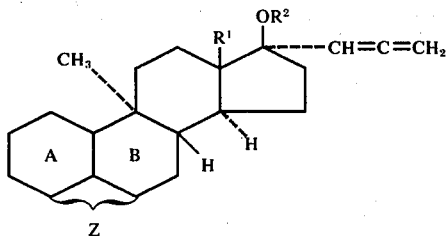

II wherein
 $R^1$ and $R^2$ are as defined above; and
 Z, embracing rings A and B and the substituents thereon, has structure

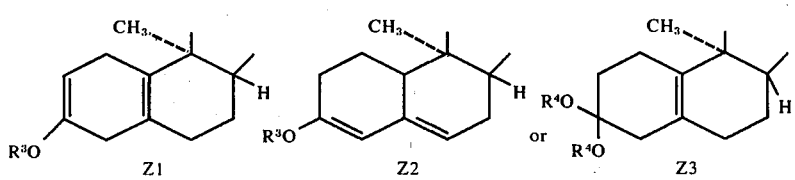

in which
 $R^3$ signifies an alkyl radical of 1 to 4 carbon atoms, preferably unbranched, e.g. methyl, and either the
 $R^4$'s each signify an alkyl radical of 1 to 4 carbon atoms, preferably unbranched, e.g. methyl,
or the
 $R^4$'s, together with the oxygen atoms to which they are attached, signify an ethylenedioxy or an n-propylenedioxy radical,
to a conventional cleavage-rearrangement deprotection reaction in an aqueous acidic medium.

Process 1 may be carried out under "vigorous" aqueous acidic conditions, i.e. at about pH value of 3 or lower, e.g. between 1 and 2, using e.g. oxalic acid, p-toluene sulfonic acid or a mineral acid, such as hydrochloric acid, for a relatively short time, e.g. less than 3 hours. Alternately, Process 1 may also be carried out under "mild" acid conditions, e.g. by use of an organic acid, such as oxalic acid, acetic acid, or generally in acid media with pH value above about 3 and preferably between 3 and 5 for a prolonged period, e.g. for a period of more than about 3 hours. Process 1 may be carried out at temperatures from, e.g. 0° to 100° C., preferably 15° to 50° C. An inert water-miscible solvent may be employed, such as a lower alkanol, e.g. methanol. Where the acid reactant is liquid it may be employed in excess to serve as solvent, e.g. acetic acid. Co-solvents may also be used.

An alternate procedure for obtaining a Compound I is to rearrange (Process 1') a Compound I':

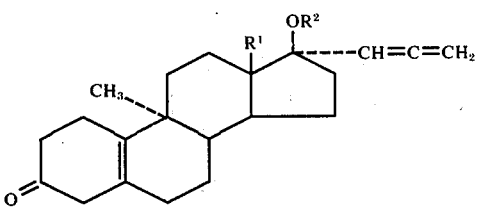

I' wherein
 $R^1$ and $R^2$ are as defined above.

Process 1'), involving rearrangement of a compound of formula I', may suitably be carried out by subjecting a compound of formula I' to acid or basic conditions. The process may be carried out under either aqueous or non-aqueous conditions.

Compounds I' are obtained from Compounds II as isolable intermediates when Process 1) is carried out under mild aqueous acidic conditions, preferably for less than 3 hrs.

Basic rearrangement may suitably be effected in an inert organic solvent, such as dioxane, methanol or ethanol. A suitable reaction temperature is from 20° to 120° C., conveniently from 20° to 30° C. or at the reflux temperature of the reaction mixture. Suitable reaction times vary, for example, from ¼ hour to 6 hours. Aqueous basic conditions may conveniently be obtained by using, for example, aqueous sodium or potassium hydroxide, preferably at a concentration of from 0.01N to 2N. Where non-aqueous conditions are employed, the basic conditions are conveniently provided by using an alkali metal lower alkoxide, e.g. sodium methoxide.

Acid rearrangement may suitably be carried out under the conditions described above in connection with process 1). However, the aqueous nature of the conditions, essential in process 1), are not essential in the present process and, accordingly, the solvent need not be water-miscible.

It is preferable to avoid subjecting a Compound I, I' or II to strongly acidic conditions, as the 17α-propadienyl group thereof may be altered under such conditions. Accordingly, it is particularly advantageous to convert a Compound II to a Compound I' by carrying out Process 1) under mild aqueous acidic conditions to obtain the corresponding Compound I' which is then converted to the corresponding Compound I by carrying out Process 1') under basic conditions.

It will be appreciated that Compounds II wherein $R^2$ is alkanoyl or acetoacetyl could be converted to a certain extent to their saponification products if subjected to aqueous basic compounds, as in Process 1'). Hence, where a Compound I wherein $R^2$ is alkanoyl or acetoacetyl is desired, it is preferable to first prepare a Compound I wherein $R^2$ is a hydrogen atom and to subsequently alkanoylate or acetoacetylate such compound, as is described hereinafter.

The compounds of the Formula I having the Formula Ib:

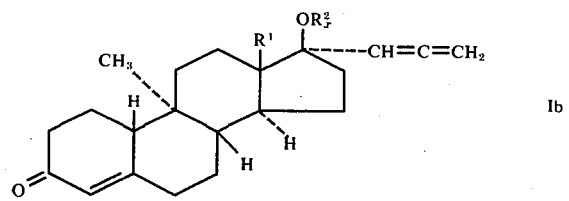

wherein $R^1$ is as defined and $R_x^2$ is acetoacetyl or alkanoyl, are obtained by conventional procedures from corresponding Compounds Ia which are the Compounds I in which $R^2$ is hydrogen.

Thus, the compounds of Formula Ib where $R^2$ is alkanoyl may be obtained by a Process A involving standard methods for acylating a tertiary hydroxy group. Strong acid conditions are preferably avoided, as mentioned above. For example, a Compound Ia may be converted into a Compound Ib where $R^2=COCH_3$ by use of acetic anhydride in which calcium hydride has been suspended.

Compounds of Formula Ib wherein $R^2$ is acetoacetyl are obtainable by a Process B involving reacting a compound of Formula Ia with a suitable reagent, e.g. diketene, under conventional conditions employed in carrying out such a reaction. For example, a Compound Ia may be reacted with diketene in an inert organic solvent, e.g. benzene or toluene or mixture thereof in the presence of a small amount of organic tertiary amine base, e.g. pyridine, at relatively low temperature, e.g. at from about −5° to +35° C.

The compounds of the Formula II in which $R^2$ is hydrogen may be prepared by following a procedure analogous to that which is described in Belgian Patent No. 742,137 and illustrated hereinater in Example 1, and which may be illustrated by Reaction Scheme A which follows in which $R^1$ and $R^3$ are as defined above, and,
either
$R^a$ and $R^b$, which may be the same or different, each signify an alkyl radical of 1 to 3 carbon atoms,
or
$R^a$ and $R^b$, together with the nitrogen atom to which they are attached, form a pyrrolidino, piperidino, or homopiperidino radical,
$R^c$ signifies an alkyl radical of 1 to 3 carbon atoms;
$X^+$ signifies the anionic residue of a mineral acid or organic sulphonic acid, other than a fluoride ion;
L is an active metal such as Li-, Na-, K-,

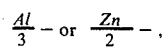

or a magnesium halide such as -MgBr or -MgI, Li being preferred;
the alkyl radicals suitable as $R^a$, $R^b$ and $R^c$ including methyl, ethyl, n-propyl and isopropyl radicals, but are preferably unbranched:

REACTION SCHEME A

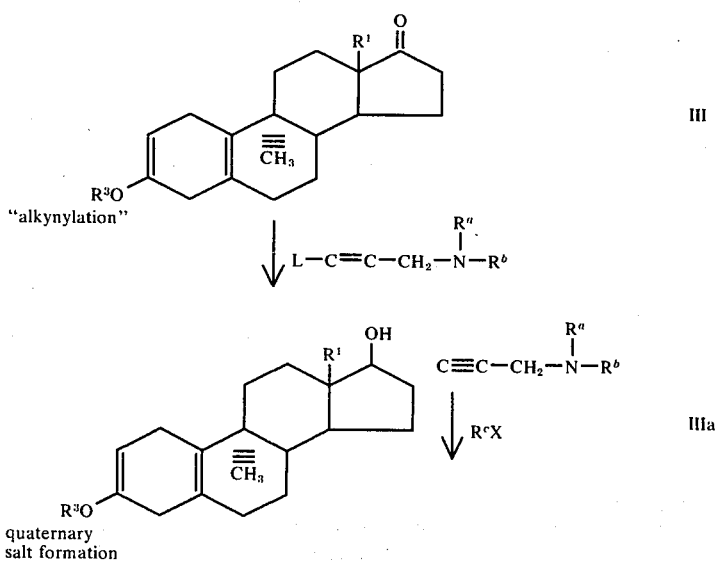

REACTION SCHEME A

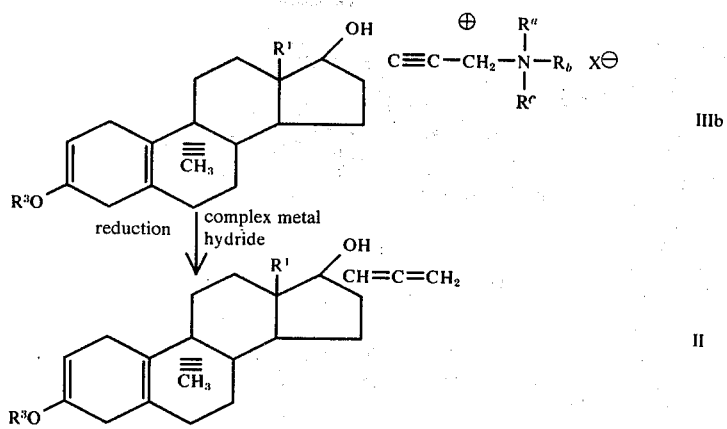

With reference to the Reaction Scheme A above, the compounds of Formula (II) are prepared by reducing a compound of Formula IIIb with a complex metal hydride in an organic medium not detrimental to the reaction.

The complex metal hydride may suitable be a hydride ion source of the formula:

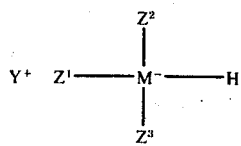

in which
Y signifies an alkali or alkaline earth metal,
M signifies aluminum, or gallium, and
$Z^1$, $Z^2$ and $Z^3$, which may be the same or different, each signify a hydrogen atom, an alkyl or alkoxy radical of 1 to 6 carbon atoms or an alkoxyalkoxy radical wherein the alkyl portion has from 1 to 6 carbon atoms and alkylene portion has from 2 to 6 carbon atoms, or a compound of formula

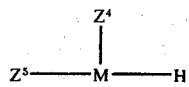

in which
M is as defined above, and
$Z^4$ and $Z^5$, which may be the same or different, each signify a hydrogen atom or an alkyl radical of 1 to 6 carbon atoms.

The alkyl and alkoxy radicals metioned above in connection with the complex hydrides are understood to include as the alkyl portion thereof methyl, ethyl, propyl, butyl, amyl, and hexyl, including isomers where such exist, but are preferably unbranched; and the alkylene radicals are understood to include ethylene, n-propylene, n-butylene, n-amylene and n-hexylene radicals.

Such complex metal hydrides are known in the art or are obtainable by procedures analogous to known methods for preparing the known compounds, and some are commercially available.

As representative of hydride ion sources may be given lithium aluminum hydride, sodium dihydro bis-(2-methoxy ethoxy) aluminate, lithium gallium hydride, magnesium aluminum hydride, lithium diisobutylmethyl aluminum hydride, lithium trimethoxy aluminum hydride and diethyl aluminium hydride; lithium aluminium hydride and sodium dihydro bis-(2-methoxy ethoxy) aluminate being preferred. In the formula given above, although, as will be appreciated, alkaline earth metals are divalent, $Y^+$ has, for the sake of simplicity, been shown as monovalent. As examples of significances of Y may be given lithium, potassium, calcium and magnesium.

The organic medium for the reduction is preferably of an aprotic nature. Suitable media include aliphatic or aromatic solvents such as benzene, toluene or pyridine, or ethers, such as diethyl ether, dioxane or tetrahydrofuran. The medium may be a single material or a mixture. Neither the particular complex metal hydride used nor the medium employed is critical. Although the temperature is not critical, the reaction may be carried out at temperatures of from −40° to +120° C., e.g. the boiling temperature of the reaction mixture, particularly at −80° . to +80° C., especially at from −10° to +50° C. Whilst higher temperatures result in faster reaction rates, lower temperatures tend to give purer products. Moisture is preferably excluded from the reaction mixture.

The compounds of Formula IIIb are prepared by a quaternization reaction by treating a compound of Formula IIIa with a compound of formula $R^cX$. The quaternization may be carried out in convention manner for preparing a quaternary ammonium salt from a tertiary amine. Although a solvent is not necessary, it is preferred that the reaction be carried out in an inert solvent, preferably acetone or acetonitrile. However, where a compound of formula $R^cX$ is liquid under the reaction conditions, such may be used in excess to serve as reaction medium. The temperature of the reaction is not critical and may suitably be carried out at −20° C. to 100° C., although it is preferred that the reaction be carried out at a temperature of from about −20° C. to +30° C., especially between about −5° C. to about +10° C.

Ions suitable as X include a monovalent ion of a halogen atom having an atomic weight of from 34 to 128; i.e., chloro, bromo, or iodo, or the residue of a sulfonic acid, e.g. of an alkylsulfonic acid such as a mesylate ion, or of an aromatic sulfonic acid, such as a tosylate ion, or the like; preferred compounds being methyl iodide and methyl p-toluenesulphonate. Accordingly, each of $R^a$, $R^b$ and $R^c$ is preferably methyl.

The compounds of Formula IIIa may be prepared by conventional means, such as the well-known Grignard technique; for example, by treating a compound of Formula III with an N,N-dialkylamino-2-propynyl lithium in an inert solvent. The preferred inert solvents are diethyl ether or tetrahydrofuran. Where an N,N-dialkylamino-2-propynyl lithium is prepared in situ in ethylenediamine, the ethylenediamine can be used as a co-solvent in the reaction. Although the temperature of the reaction is not critical, it is preferred that the process be carried out at temperatures between about −30° C. to +50° C. especially between about −20° C. to about +30° C.

It will be appreciated that ring A in a protected form is stable under those basic conditions encountered during the conversion of a Compound III to a Compound II, and that such conversion reactions being confined to the region of the 17-carbon atom, the remaining portions of a particular steroidal structure will be retained.

The Compounds II in which $R^2$ is hydrogen may be employed to obtain the other Compounds II in which $R^2$ is other than hydrogen. Thus, the compounds of Formula I in which $R^2$ is methyl are desirably prepared from the compounds of Formula II in which $R^2$ is methyl and such compounds of the Formula II may be obtained in a manner known per se, for instance by treating a Compound II in which $R^2$ is hydrogen, at a temperature of about −80° C. to 30° C. with 1–1.2 equivalents of strong base (e.g. $NaNH_2$ or $KNH_2$ in liquid ammonia or $LiCH_3$ in ether) to form a 17-O-anion of Compound II, and treating the latter, in the same mixture, with 1–50 equivalents of methyl iodide.

The "A-ring protected" Intermediates (III) are obtainable from the corresponding 13-alkyl-3-alkoxy-9α-methylgona-1,3,5-trien-17-ones (Compounds VI).

For example, a Compound VI may be reduced at the 17-carbonyl function to obtain the corresponding 17-hydroxy-substituted Compound V, which in turn may be subjected to the well-known Birch reduction to obtain the corresponding 13-alkyl-3-alkoxy-9α-methyl-gona-2,5-dien-17β-ol (a Compound IV). The compound IV is then subjected to oxidation wherein the 17-hydroxy function is oxidized to a carbonyl function, thus obtaining a Compound III. The oxidation may be achieved by conventional means for oxidizing a secondary hydroxy function to oxo, e.g. by employing the well-known Oppenauer oxidation technique.

Alternatively, a Compound VI may be converted directly to a Compound IV by subjection to Birch Reduction conditions.

The preparation of a Compound III via Process 2 is conveniently represented by the following Reaction Scheme B which follows wherein $R^1$ and $R^3$ are as defined above:

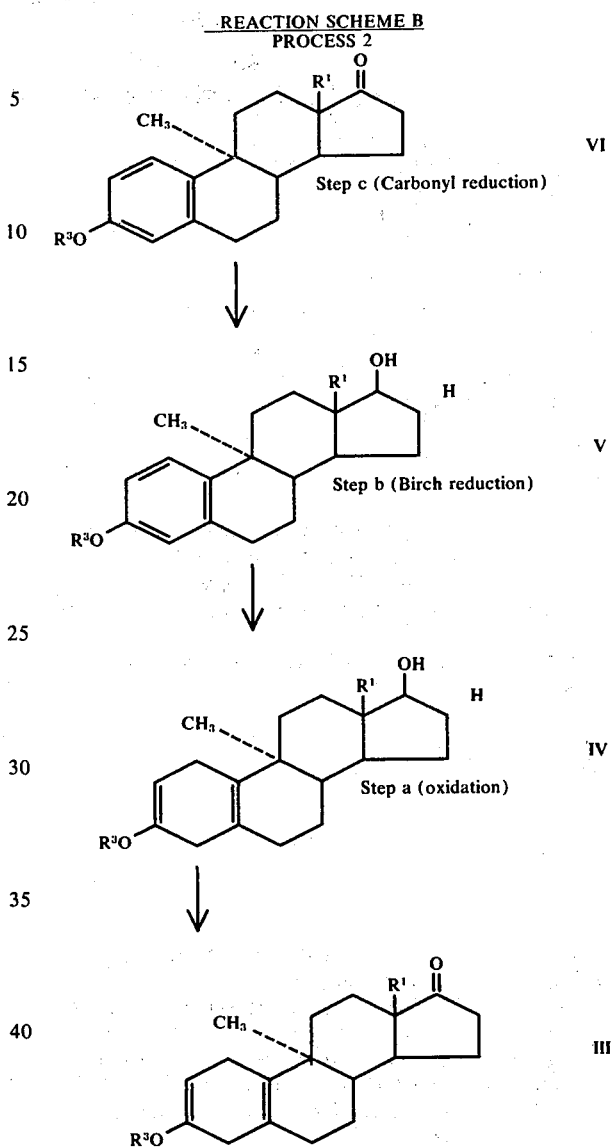

The conversion of a Compound IV to the corresponding Compound III, i.e. (Step a) may be accomplished by conventional means for oxidizing a secondary aliphatic hydroxy to a carbonyl, for example, by employing the so-called Oppenauer oxidation, which broadly involves oxidizing a hydroxy function in the presence of a metallic alkoxide and a ketone, e.g. aluminum isopropoxide and 2-butanone, e.g. at temperatures of about 60° to 130° C., in a suitable solvent, such as benzene toluene and the like.

Step b, i.e. the reduction of ring A of an aromatic structure, i.e. having unsaturation at the 1,3, and 5(10) positions of a Compound V to a 2,5(10) (a Compound IV) may be accomplished by employing the so-called Birch reduction, which broadly involves use of a light metal and tert.-butanol, e.g. lithium, in liquid ammonia at reduced temperatures (sufficient to maintain the ammonia in a liquid state); no solvent is required as the ammonia can serve as the reaction medium, but can be used, e.g. benzene or tetrahydrofuran.

Step c, i.e. the reduction of a 17-carbonyl function of a Compound VI to a 17β-hydroxy (Compound V), may be accomplished by treatment in the conventional manner with a light metal hydride, e.g. a NaBH₄ or LiAlH₄ under conditions conventionally applied in carrying out such a reduction, e.g. ethanol or ethanol-methylene chloride for NaBH₄ and tetrahydrofuran for LiAlH₄.

The starting material for Process 2, i.e. a Compound VI, may be conveniently obtained from starting materials (Compounds A) by a series of steps, comprising Process 3. Process 3 is represented in Reaction Scheme C as follows; wherein $R^1$ and $R^3$ are as defined:

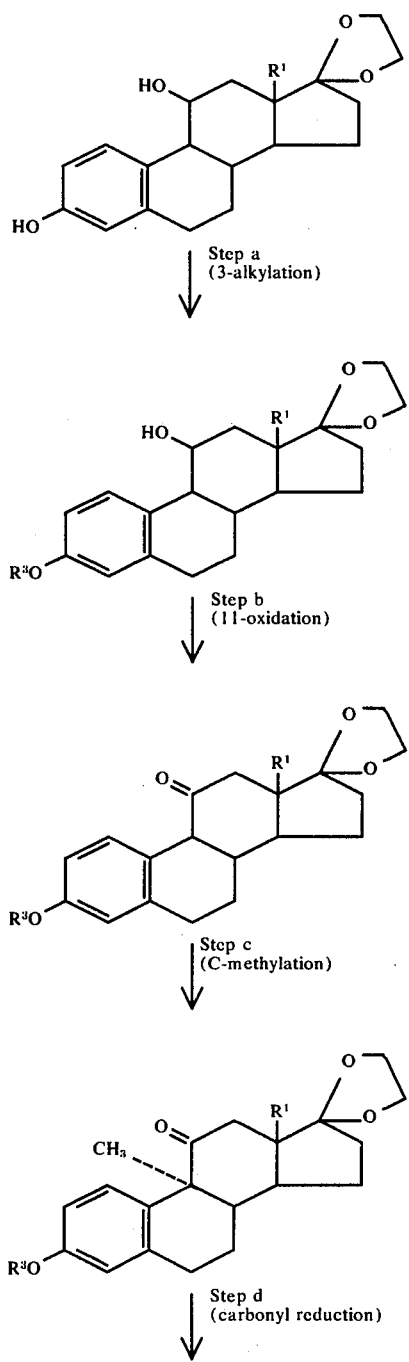

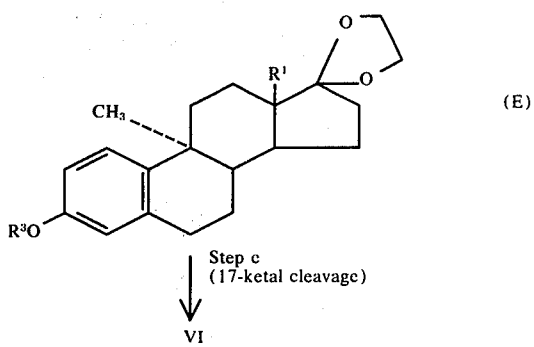

In process 3, as shown in Reaction Scheme C, above, Step a (3-alkylation may be effected in manner conventional for the etherification of a phenolic hydroxy function using an $R^3$-contributing alkylating agent. The alkylating agent may, for example, be an alkyl iodide having from 1 to 4 carbon atoms, and the process conveniently carried out under basic conditions, provided, for example, by the presence of anhydrous potassium carbonate. Suitably, the process is carried out in an inert organic solvent, for example a lower alcohol such as methanol. The reaction temperature may for example be from 60° to 100° C., although preferably the reaction is performed at the reflux temperature of the reaction medium. When an alcohol is used as solvent, it preferred that the alkyl moieties of the alcohol and the alkylating agent be the same.

In Step b, a Compound B, i.e. a 17-ethylenedioxy-3-alkoxygona-1,3,5(10)-11β-hydroxy-triene is oxidized to convert the 11-hydroxy position thereof to a carbonyl function. The oxidation (Step b) may be carried out by conventional means for the oxidation of a secondary alkyl hydroxy function to a carbonyl function, e.g. the so-called Moffat oxidation.

In Step c, the C-methylation to obtain a 17-ethylenedioxy-3-alkoxy-9α-methylgona-1,3,5(10)-trien-11-one, may be carried out by reacting a Compound C with a methylating agent in the presence of a strong base at a temperature of from about −20° to 60° C., in a suitable solvent.

The methylating agent, i.e. a Compound Q, may be represented by the formula:

CH₃-Z  (Q)

wherein
Z is a nucleofugal leaving group, e.g. a halogen atom having an atomic weight of from 35 to 127, tosylate, and -O-S-O₃-CH₃.

The strong base, i.e., a compound S, may be conveniently represented by the formula:

M'-A  (S)

wherein
A is lower alkoxy, e.g., having from 1 to 6 carbon atoms, such as methoxy, ethoxy, propoxy, butoxy, pentoxy and hexoxy and their isomeric forms, or the anion -NH₂, -H or -CH₂SO-CH₃, and the like; and
M' is an alkali metal, e.g. Na or K.

Step c should be carried out in a suitable solvent, e.g., t-butanol or dimethyl sulfoxide; however, where the methylating agent is liquid under the reaction conditions, excess methylating agent may serve as solvent.

It is preferred to employ the methylating agent in excess, particularly in such a large excess that it serves as solvent, i.e., reaction medium, e.g., of the order of from about 10 to 200 fold excess.

Reaction conditions conventionally applied to C-methylation reactions are therefore applied.

In Step d), a 17-ethylenedioxy-3-alkoxy-9α-methyl-gona-1,3,5(10)-trien-11-one is reduced to its corresponding Compound E, i.e. the carbonyl function at the 11-position is converted to a methylene unit, by means conventionally employed for reducing a carbonyl to a methylene structure, e.g. the well-known Wolff-Kishner reduction.

In Step e), the ethylenedioxy function at the 17-position of a Compound E is then acid-cleaved to yield a Compound III. Step e) may be carried out in the conventional manner for cleaving a ketal linkage, e.g. by refluxing with hydrochloric acid or p-toluene sulfonic acid in methanol.

Compounds A are either known and obtainable by methods described in the literature, or where not known may be obtained by methods analogous to those for preparing the known compounds.

Preparation of compounds which serve as intermediates in this invention, but are not themselves part of this invention, e.g. Compounds VI and III, are described in Belgian Patent Nos. 753,779 and 771,111.

As will be appreciated, the Z structures of the compounds used in the present invention are conventional base-stable protected forms of A B ring steroidal unsaturated structures having a 3-oxo function. The preparation of such Z structures is well known in the art. For example, compounds having forms Z2 and Z3 may, in known manner, be prepared from compounds having form Z1. Accordingly, compounds of Formula VII, wherein Z has structure Z2 or Z3, may be obtained, in manner known per se, from compounds of Formula VII in which Z has the structure Z1. It will be further appreciated that the 17-ethylenedioxy group of Compound A in Reaction Scheme C could be substituted by another protective ketal, such as an n-propylenedioxy radical.

Alternative to the above-described method of preparation of Compounds I, these compounds may be prepared by a procedure involving a series of steps, which are conveniently represented by Reaction Scheme D, below, in which $R^1$, $R^3$, $R^a$, $R^b$, $R^c$ and X are as defined above:

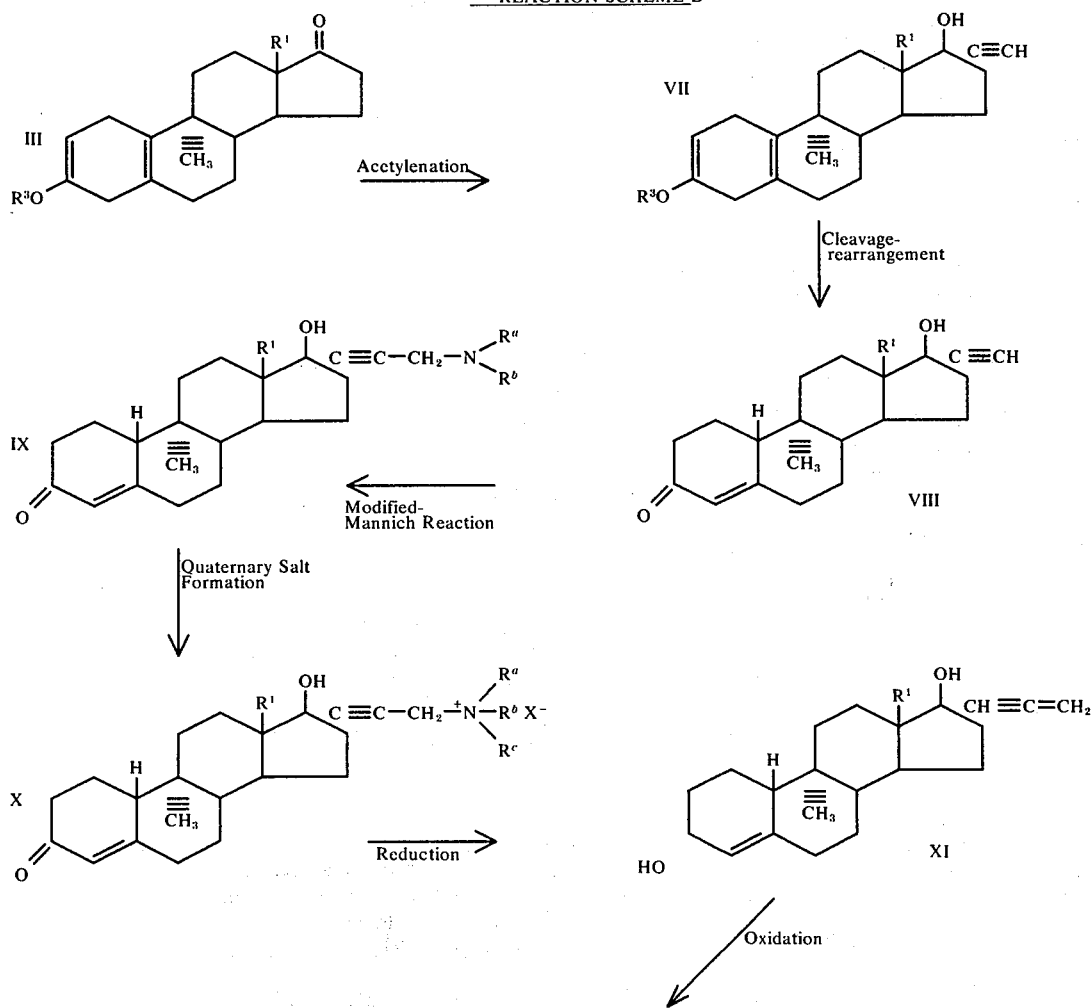

-continued
REACTION SCHEME D

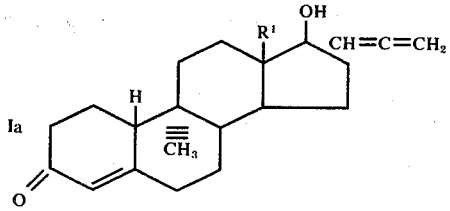

With reference to Reaction Scheme D, Compounds III are obtainable as described above. The preparation of a Compound VII entails reaction at the 17-oxo function of a Compound III, with an acetylenating agent, e.g. a suitable Grignard-type reagent to obtain the 17α-ethynyl, 17β-hydroxy analog thereof, i.e. the corresponding Compound VII. The acetylenation reaction may be carried out in a conventional manner, the adaptation of such general reaction being well within the skill of persons skilled in the art, e.g. by use of lithium acetylide-ethylenediamine complex. The conversion of a Compound VII to its corresponding Compound VIII involves cleavage-rearrangement at the A-ring, and may be carried out in the same manner as described above for process 1.

Compounds VIII are converted to their corresponding Compounds IX, i.e. steroidal Mannich bases, by reaction with an aminomethanol, of formula

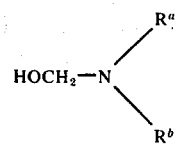

in which $R^a$ and $R^b$ are as defined above, in the presence of a monovalent coinage metal ion, i.e., Cu(I), Au(I) or Ag, preferably Cu(I). The reaction is conveniently carried out at a temperature of from 20° to 80° C., preferably from 20° to 30° C. The reaction may be carried out in a solvent, e.g. in an ether such as diethylether, tetrahydrofuran or p-dioxane, and in the presence of a salt, adduct or complex of copper, silver or gold capable of providing monovalent ions under the reaction conditions. As Examples of suitable salts may be given cuprous chloride, cuprous bromide, cuprous nitrate, cuprous acetate, silver or gold (I) chloride or bromide, or silver nitrate; cuprous chloride being preferred. As Examples of complexes may be given copper, silver and gold cyanides. Where any of the reactants is liquid under the reaction conditions, such may be used in excess to serve as reaction medium. A preferred solvent is p-dioxane. A preferred aminomethanol is dimethylaminomethanol.

The quaternization of a Compound IX to its corresponding Compound X, may be carried out in the same manner as described above for obtaining a Compound IIIb.

The reduction of a Compound X to its corresponding Compound XI may be carried out in the same manner as described above for obtaining a Compound II. It will be noted that concomitant with the reaction in the area of the 17-carbon atom yielding an allene function, the 3-oxo function at the A-ring is reduced to a hydroxy function, yielding a mixture of 3α, 17β-diols and 3β,17β-diols. In the subsequent oxidation step, the 3-hydroxy function of a Compound XI is oxidized to an oxo function regardless of its isomeric configuration. Hence, the proportion of 3α- to 3β-hydroxy isomers constituting a Compound XI employed in this procedure is unimportant.

In the oxidation of the 3-hydroxy function (of a Compound XI) to an oxo function (to obtain a Compound I) may be carried out in conventional manner. Suitable oxidizing agents include quinones, such as p-benzoquinone, chloranil or 2,3-dicyano-5,6-dichlorobenzoquinone, (DDQ) and activated manganese dioxide, preferably 2,3-dicyano-5,6-dichlorobenzoquinone. The oxidation is preferably carried out at a temperature of from 10° to 50° C., more preferably from 20° to 30° C. Preferably an inert solvent, e.g. a cyclic ether such as dioxane, or a tertiary alkanol such as t-butanol, is employed.

Reagents used in the processes above-described are known and may be prepared by methods described in the literature, or where not known, may be prepared by methods analogous to those for preparing the known compounds. Many of these compounds are obtainable commercially.

If desired, a Compound IIIa (of Reaction Scheme A), i.e. an intermediate for the preparation of Compounds II, wherein $R^2$ is a hydrogen atom and Z is of type Z1, may be obtained by reacting a Compound VII under the modified-Mannich reaction conditions described above, (in connection with Reaction Scheme D), thus affording an additional alternative procedure for obtaining the Compounds I and I' of this invention.

The compounds of Formula I are useful because they possess pharmacological properties in animals. In particular, such compounds exhibit progestational activity, and are particularly useful as fertility control agents in warm-blooded animals, including regulating estrus or the menstrual cycle in mammals. The progestational activity is indicated by the well-known Clauberg test; the method basically described in Endocrinology 63 (1958) 464 wherein a rabbit is given 0.005 to 1.0 milligrams of active agent. A particularly preferred compound I is 9α-methyl-17β-propadienylestra-4-en-17-ol-3-one.

These compounds may be combined with a pharmaceutically acceptable carrier or adjuvant. They may be administered orally or parenterally. The dosage will vary depending upon known factors such as the mode of administration utilized, the particular compound employed and the nature of the host. However, in general, satisfactory results are obtained in warm-blooded animals, i.e. birds and mammals, when the compounds are administered at a daily dosage of from about 0.005 milligram to 50 milligrams. This daily dosage may be administered in sustained release form. As will be appreciated by those skilled in the art, that the daily dosage level is recognized as not directly related to body weight. Dosage forms suitable for internal administration comprise from about 0.005 mg. to 50 mg. of the compound in admixture with a solid or liquid pharmaceutical carrier or diluent; solid forms, e.g. capsules or tablets being preferred.

For example, Compounds I, as particularly represented by 9α-methyl-17β-propadienylestra-4-en-17β-ol-3-one, are especially useful in estrus regulation in swine at daily doses more suitably of from about 3 to 30 milligrams, preferably from about 4 to 15 milligrams, based on the observation that cystic follicles are not formed. This property is particularly surprising in view of the fact that the formation of cystic follicles is a common result in attempts to regulate estrus in swine with other steroids.

The Compounds I' possess a combination of estrogenic and progestational activity and are therefore useful in controlling fertility of warm-blooded animals and regulating estrus or the menstrual cycle of mammals. Said progestational activity is indicated by the pertinent method described above while the estrogenic activity is indicated by observing for cornification of vaginal epithelium of adult female ovariectomized white rats scored according to the method of Biggers and Claringbold, when said animals are given from 0.05 to 10 milligrams of active agent. For such uses Compounds I' may be administered in the same manner and forms as described above for Compounds I, but at a daily dosage of from about 0.05 mg. to 50 mg.; unit dosage forms therefore having from about 0.05 mg. to 50 mg. of a Compound I'.

A representative formulation suitable for oral administration is a capsule (250 mg.) prepared by standard techniques which contains the following:

| Ingredient | Weight (mg.) |
|---|---|
| 9α-methyl-17α-propadienylestra-4-en-17β-ol-3-one | 0.5 |
| Inert solid diluent (starch, lactose, kaolin) | 249.5 |

The following examples are provided as illustrative of the invention; all temperatures are Centigrade and room temperature 25° C., unless indicated otherwise.

EXAMPLE 1

9alpha-methyl-17alpha-(propa-1',2'-dienyl)-17beta-hydroxyestra-4-en-3-one

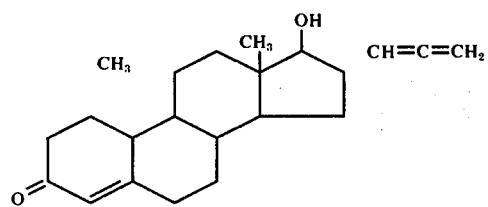

STEP A:

17-Ethylenedioxy-11β-hydroxy-3-methoxyestra-1,3,5(10)-triene (a compound by process 3, step a).

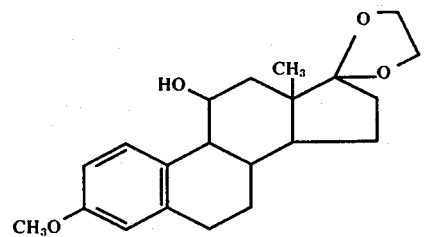

A mixture of 15 g of 17-ethylenedioxyestra-1,3,5(10)trien-3,11β-diol and 30 g of anhydrous potassium carbonate in 75 ml of methanol and 60 ml of methyl iodide is stirred and heated under reflux for 3 hours. The mixture is then cooled and diluted by the addition of 200 ml of water. The methanol and methyl iodide are removed by distillation under reduced pressure and the aqueous residue is extracted twice with methylene chloride. The combined organic extracts are washed with saturated sodium chloride solution and dried over sodium sulfate. Removal of the solvent gives a residue which is crystallized from ether to yield 17-ethylenedioxy-11β-hydroxy-3-methoxyestra-1,3,5(10)-triene, m.p. 125° 14 126° C.

STEP B:

17-Ethylenedioxy-3-methoxyestra-1,3,5(10)-triene-11-one (a compound by process 3, step b).

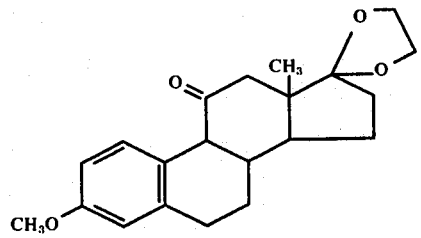

To a stirred solution of 5.13 g of 17-ethylenedioxy-11β-hydroxy-3-methoxyestra-1,3,5(10)-triene in 25 ml of dimethylsulfoxide and 25 ml of benzene is added 3 ml of pyridine and 9.3 g of N,N-dicyclohexylcarbodiimide. This mixture is then cooled and 1.5 ml of dichloroacetic acid is added. The whole is next stirred at room temperature for 1½ hours. It is diluted by the addition of 50 ml of ether and a solution of 4 g of oxalic acid in 10 ml of methanol is added dropwise. The resulting suspension is stirred for 40 minutes at room temperature and then filtered. The filtrate is concentrated to dryness and distributed between methylene chloride and a 10% aqueous solution of sodium bicarbonate. The organic phase is washed with water and dried ($Na_2SO_4$) before being evaporated to dryness under reduced pressure. The residue is placed on a column of silica-gel and eluted with chloroform containing various percentages of methanol. The fractions eluted with chloroform containing 5% of methanol are combined and evaporated to yield a residue which is crystallized from hexane/ether (1:1). Thus is obtained 17-ethylenedioxy-3-methoxyestra-1,3,5(10)-trien-11-one, m.p. 122° – 123° C.

STEP C:
17-Ethylenedioxy-3-methoxy-9α-methylestra-1,3,5(10)-trien-11-one (a compound by process 3, step c).

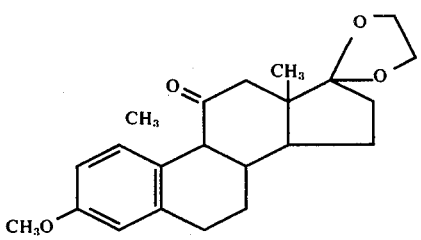

To a stirred, ice cooled solution of 10.5 g of 17-ethylenedioxy-3-methoxyestra-1,3,5(10)-trien-11-one in 300 ml of methyl iodide under an atmosphere of nitrogen is added, over 10 minutes, 120 ml of a 1.1 molar solution of potassium tert.-butoxide in t-butyl alcohol. The temperature is allowed to rise to room temperature and the mixture is then stirred for 18 hours. It is next poured onto 500 ml of water and extracted with methylene chloride, twice. The combined organic extracts are washed with water and dried over sodium sulfate. Removal of the solvent gives an oil which is crystallized from ether to yield 17-ethylenedioxy-3-methoxy-9α-methylestra-1,3,5(10)-trien-11-one, m.p. 142° – 145° C.

STEP D:
17-Ethylenedioxy-3-methoxy-9α-methylestra-1,3,5(10)-triene (a compound by process 3, step d).

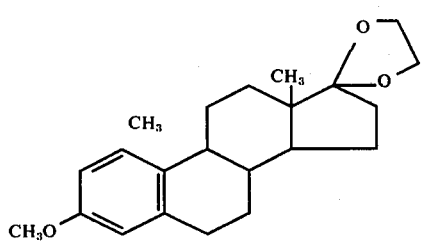

A mixture of 534 mg of 17-ethylenedioxy-3-methoxy-9α-methylestra-1,3,5-(10)-trien-11-one, 1 g of hydrazine dihydrochloride and 5 g of hydrazine hydrate in 35 g of triethyleneglycol is heated to a temperature of 130° and maintained there for 2½ hours. After this time, 1.8 g of potassium hydroxide pellets is added and the temperature raised to 210°. This temperature is also maintained for 2½ hours whilst a mixture of hydrazine and water is slowly allowed to distill out. The reaction mixture is cooled and diluted with water affording a precipitate which is collected by filtration. The solid is dissolved in methylene chloride and the organic solution is dried over sodium sulfate. Removal of the solvent leaves a residue which is crystallized from hexane-ether to yield 17-ethylenedioxy-3-methoxy-9α-methylestra-1,3,5(10)-triene, m.p. 115° C.

STEP E: 9α-Methylestrone methyl ether

To a warm solution of 220 mg of 17-ethylenedioxy-3-methoxy-9α-methylestra-1,3,5(10)triene in 5 ml of methanol is added 1 ml of 2N hydrochloric acid solution and the mixture is heated under reflux for 5 minutes. On cooling, crystals are precipitated and these are isolated by filtration. The crystalline solid is washed with a small quantity of ether to yield 9α-methylestrone methyl ether, m.p. 190° – 192° C.

STEP F.: Preparation of 9alpha-Methyl-estra-2,5(10)-dien3,17)-dien-3 methyl ether.

A solution of 6.0 g. of 9alpha-methylestrone methyl ether in 90 ml of tetrahydrofuran and 90 ml of 1-butanol is added to 200 ml of ammonia under reflux. A total of 2.8 g of lithium is then added in portions over 10 min and the resulting blue solution is stirred under reflux for 6 hrs. The ammonia is allowed to evaporate overnight and 50 ml of methanol is added to the residue followed by 300 ml of saturated aqueous sodium chloride and 200 ml of benzene. The two phases are separated and the organic layer is washed with saturated aqueous sodium chloride, dried over anhydrous sodium sulphate and evaporated to give a residue which is crystallized from methanol. Thus is obtained 9alpha-methylestra-2,5(10)-dien-3,17-diol 3 methyl ether m.p. 116° – 120°.

STEP G.: Preparation of 3-Methoxy-9alpha-methyl-estra-2,5(10)-dien-17-one.

A mixture of 5.0 g of 9alpha-methylestra-2,5(10)-dien-3,17-diol 3 methyl ether and 4.5 g of aluminum isopropoxide in 45 ml of benzene and 45 ml of 2-butanone is stirred and refluxed for 22 hrs., using a water separator. After cooling, the reaction mixture is added to 100 ml. of 2N sodium hydroxide solution and a further 50 ml. of benzene are added. The organic layer is separated, washed with water and saturated sodium chloride and dried over anhydrous sodium sulphate. Removal of the solvent gives a residue which is crystallized from ether/hexane, 1/1 yielding 3-methoxy-9alpha-methyl-estra-2,5(10)-dien-17-one, m.p. 155°–158°, which may be used in Step H, below. Recrystallization from ether yields a product of m.p. 175°–177°.

STEP H.: Preparation of 17alpha-N,N-Dimethylamino-propynyl-9alpha-methyl-estra-2,5(10)-dien-3,17beta-diol-3-methyl ether.

A total of 2.2 g. of lithium is added portionwise to 150 ml. of ethylenediamine, stirred and maintained at a temperature of 50°–60° under nitrogen. After the addition is complete the blue solution is heated to 75°–85° for 1½ hrs. when a pale yellow reaction mixture is obtained. This is then cooled to 10° and 24 g. of N,N-dimethylamino-2-propyne is added over 5 min. Stirring is continued at room temperature for 1 hr., when a solution of 3.2 g. of 3-methoxy-9alpha-methyl-estra 2,5(10)-dien-17-one in 40 ml of tetrahydrofuran is added. The mixture is now stirred at room temperature for 16 hrs. After cooling (ice/water) 200 ml. of saturated sodium chloride are added under nitrogen, followed by 300 ml of benzene. The two layers are separated, the aqueous extracted three times with benzene and the combined organic phases are washed with saturated sodium chloride before being dried over anhydrous sodium sulphate. After removal of the solvent there is obtained the product as an oil which is used in the subsequent step.

STEP I.: Preparation of the Quaternary Ammonium Salt.

To a solution of 3.8 g. of 17alpha-N,N-dimethylaminopropynyl-9-alpha-methyl-estra-2,5(10)-dien-3,17beta-diol 3 methyl ether in 90 ml of acetone is added 30 ml of methyl iodide. The solution is kept at a temperature of 5° for 18 hrs. during which time a crystalline precipitate forms. This is filtered off and recrystallized from methanol/acetone, 1/5, to yield the product m.p. 240–243 (dec.).

STEP J.: Preparation of 9alpha-methyl-17alpha-propa-1', 2'-dienyl-estra-2,5(10)-dien-3,17β-diol 3 methyl ether.

To a suspension of 3.3 g. of the above iodide salt in 100 ml of anhydrous tetrahydrofuran, under ice cooling is added 10 ml of a 70% solution of sodium di(methoxyethoxy) aluminum hydride* in benzene diluted with 25 ml of tetrahydrofuran. The reaction mixture is allowed to warm to room temperature and stirred for a total of 2 hrs. by which time solution is complete. Water is then added to decompose the excess hydride and the tetrahydrofuran is removed under reduced pressure. The aqueous residue is extracted with methylene chloride and the organic phase is dried over anhydrous sodium sulphate. After removal of the solvent there is obtained the product, 9alpha-methyl-17alpha-propa-1',2'-dienyl-estra-2,5(10)-dien-3,17beta-diol 3 methyl ether as an oil sufficiently pure for use in the next step. This product is alternatively named 3-methoxy-9α-methyl-17α-propadienylestra-2,5(10)-dien-17β-ol, which can be crystallized from ether/hexane (⅛) to obtain a refined product of m.p. 86° to 90° C.

* Alternatively known as sodium dihydro bis-(2-methoxy ethoxy) aluminate.

STEP K.: Preparation of 9alpha-methyl-17alpha-(propa-1', 2'-dienyl)-17beta-hydroxy-estra-4-en-3-one.

To a solution of 600 mg of 9α-methyl-17α-(propa-1',2'-dienyl)-estra-2,5(10)-dien-3,17beta-diol 3 methyl ether in 10 ml of methanol is added 5 drops of conc. hydrochloric acid and the mixture is left at room temperature for 1½ hrs. It is then diluted with ice/water and a saturated aqueous solution of sodium bicarbonate is slowly added until the mixture is no longer acidic. It is then extracted with ether and the organic solution is dried over anhydrous sodium sulphate. Removal of the solvent gives a residue which is crystallized from ether to yield 9alpha-methyl-17-alpha(propa-1',2'-dienyl)-17beta-hydroxy-estra-4-en-3-one, m.p. 218°–220°. The radical propa-(1',2'-dienyl) is also alternately herein designated propadienyl.

Repeating the steps of this example but using in place of the 17-ethylenedioxyestra-1,3,5(10)-trien-3,11β-diol, used in Step A, an approximately equivalent amount of:
a. 13-ethyl-17-ethylenedioxygona-1,3,5(10)-trien-3,11β-diol; or
b. 17-ethylenedioxy-13-n-propylgona-1,3,5(10)-trien-3,11β-diol;
there is obtained:
a. 13-ethyl-9α-methyl-17α-propadienylgona-4-en-17β-ol-3-one; or
b. 9α-methyl-17α-propadienyl-13-n-propylgona-4-en-17β-ol-3-one.

EXAMPLE 2

17β-acetoxy-9α-methyl-17α-propadienylestra-4-en-3-one

A mixture of 0.050 g. of calcium hydride in 5 ml. of acetic anhydride is refluxed for 1 hour then 0.5 g. of 9α-methyl-17α-propadienylestra-4-en-17α-ol-3-one is added and refluxing continued for three more hours. After cooling, the mixture is poured on ice and extracted with methylene chloride. The methylene chloride solution is washed with aqueous saturated sodium bicarbonate and then water, dried over anhydrous sodium sulfate and evaporated to give the 17β-acetoxy-9α-methyl-17α-propadienylestra-4-en-3-one product.

Repeating the above-described procedure, but using in place of the 9α-methyl 17α-propadienylestra-4-en-17β-ol-3-one an approximately equivalent amount of (a) 3-methoxy-9α-methyl-17α-propadienylestra-2,5(10)-dien-17β-ol or (b) 13-ethyl-9α-methyl-17α-propadienylgona-4-en-17β-ol-3-one, there is similarly obtained: (a) 17β-acetoxy-3-methoxy-9α-methyl-17α-propadienylestra-2,5(10)-diene or (b) 17β-acetoxy-13-ethyl-9α-methyl-17α-propadienylgona-4-en-3-one.

EXAMPLE 3

17β-Acetoacetoxy-9α-methyl-17α-propadienylestra-4-en-3-one

To a solution of 1.0 g. of 9α-methyl-17α-propadienyl-estra-4-en-17β-ol-3-one (Example 1) in a mixture of 18.5 ml. of benzene, 9.25 ml. of toluene and 0.23 ml. of pyridine, there is dropwise added, at 0°, 1.8 ml. of diketene, dissolved in 9 ml. of benzene. The mixture is then kept at 25° for 3 hours. The product is isolated by washing the mixture with ice-cold 0.1 N sodium hydroxide and water, drying over anhydrous sodium sulfate, and evaporating to dryness to obtain the title product.

Repeating the above-described procedure, but using in place of the 9α-methyl-17α-propadienylestra-4-en-17β-ol-3-one used therein an approximately equivalent amount of 13-ethyl-9α-methyl-17α-propadienylgona-4-en-17β-3-one, there is similarly obtained 17β-acetoacetoxy-13-ethyl-9α-methyl-17α-propadienyl-gona-4-en-3-one.

EXAMPLE 4

17β-Methoxy-9α-methyl-17α-propadienylestra-4-en-3-one

STEP A - 3,17β-dimethoxy-9α-methyl-17α-propadienylestra-2,5(10)-diene.

To a solution of lithium amide in liquid ammonia (prepared from 73.5 mg. Li and 25 ml. of NH₃) there is added a solution of 3.3 g. of 9α-methyl-3-methoxy-17α-propadienyl-estra-2,5(10)-dien-17β-ol (obtainable by step J of Example 1) in 50 ml. of ether. After two hours at refluxing ammonia temperature, 2.5 g. of methyl iodide is added and the ammonia allowed to escape. Addition of 50 ml. of water and separation of the ether phase (and ether washup) followed by the evaporation of the dried ethereal solutions yields 3,17β-dimethoxy-9α-methyl-17α-propadienylestra-2,5(10)-diene.

STEP B -
17β-methoxy-9α-methyl-17α-propadienylestra-4-en-3-one

Carrying out the procedure of step K of Example 1, but using the product of step A of this example in place of the 9α-methyl-17α-propadienylestra-2,5(10)-dien-3,17β-diol-3-methyl ether used therein there is obtained 17β-methoxy-9α-methyl-17α-propadienylestra-4-en-3-one.

EXAMPLE 5
9α-Methyl-17α-propadienylestra-4-en-17β-ol-3-one

STEP A:
9α-Methyl-17α-propadienylestra-5(10)-en-17β-ol-3-one (a compound of Formula I')

A solution of 12 g. of 3-methoxy-9α-methyl-17α-propadienylestra-2,5(10)-dien-17β-ol (obtainable by Step J of Example 1) in 80 ml. of glacial acetic acid and 20 ml. of water, is stirred at room temperature for 2 hrs. The reaction mixture is then poured on to ice, and then neutralized with 1 N aqueous sodium hydroxide. The crude title product which precipitates is extracted with methylene chloride. The combined extracts are washed with water, dried over anhydrous sodium sulphate, and then evaporated under vacuum to obtain the crude title product as a residue, which is then recrystallized from ether/hexane (1:1), to yield 9α-methyl-17α-propadienylestra-5(10)-en-17β-ol-3-one, m.p. 129°–131°.

STEP B:
9α-Methyl-17α-propadienylestra-4-en-17β-ol-3-one

Carrying out the procedure of Step K of Example 1, but using in place of the 3-methoxy-9α-methyl-17α-propadienylestra-2,5(10)-dien-17β-ol, used therein, an approximately equivalent amount of 9α-methyl-17α-propadienylestra-5(10)-en-17β-ol-3-one, there is obtained 9α-methyl-17α-propadienylestra-4-en-17β-ol-3-one.

Repeating the procedure of Step A of this example, but using in place of the 3-methoxy-9α-methyl-17α-propadienylestra-2,5(10)-dien-17β-ol used therein, an approximately equivalent amount of: (a) 13-ethyl-3-methoxy-9α-methyl 17α-propadienylgona-2,5(10)-dien-17β-ol, (b) 3,17β-dimethoxy-9α-methyl-17α-propadienylestra-2,5(10)-diene, or (c) 3-methoxy-9α-methyl-17α-propadienyl-13-n-propylgona-2,5(10)-diene, there is similarly obtained (a) 13-ethyl-9α-methyl-17α-propadienylgona-5(10)-en-17β-ol-3-one, (b) 17β-methoxy-9α-methyl-17α-propadienylestra-5(10)-en-3-one, or (c) 9α-methyl-17α-propadienyl-13-n-propylgona-5(10)-en-17β-ol-3-one.

EXAMPLE 6
9α-Methyl-17α-propadienylestra-4-en-17β-ol-3-one

To 1 g. of 9α-methyl-17α-propadienylestra-5(10)-en-17β-ol-3-one (obtainable by Example 5 Step A, above) in 10 ml. of methanol is added 100 mg. of sodium methoxide, and the resulting mixture stirred at room temperature for 1 hour. 20 ml. of water are then carefully added to the reaction mixture and the crude product, which precipitates, is filtered off and recrystallized from ether to yield the title product.

Repeating the procedure of this example, but using in place of the 9α-methyl-17α-propadienylestra-5(10)-en-17β-ol-3-one, an approximately equivalent amount of (a) 13-ethyl-9α-methyl-17α-propadienylgona-5(10)-en-17β-ol-3-one or (b) 9α-methyl-13-n-propyl-17α-propadienylgona-5(10)-en-17β-ol-3-one, there is similarly obtained (a) 13-ethyl-9α-methyl-17α-propadienylgona-4-en-17β-ol-3-one or (b) 9α-methyl-17α-propadienyl-13-n-propylgona-4-en-17β-ol-3-one.

EXAMPLE 7

Tablets and capsules containing the ingredients indicated below may be prepared by conventional techniques and are useful in controlling fertility in the manner described above:

| Ingredients | Weight (mg.) | | |
|---|---|---|---|
| | (a) Tablet | (b) Capsule | (c) Capsule |
| 9α-Methyl-17α-propadienylestra-4-en-17β-ol-3-one | 0.5 | 0.5 | 6 |
| Tragacanth | 10 | — | — |
| Lactose | 247.0 | 299.5 | 494 |
| Corn starch | 25 | — | — |
| Talcum | 15 | — | — |
| Magnesium stearate | 2.5 | — | — |
| Total | 300.0 mg. | 300.0 mg | 500 mg. |

EXAMPLE 8

The following pharmaceutical composition is formulated with the indicated amount of active agent using conventional techniques. The injectable suspension represents a formulation useful in controlling fertility in the manner described above.

| Ingredients | Weight % |
|---|---|
| 9α-Methyl-17α-propadienylestra-4-en-17β-ol-3-one | 1.0 |
| Sodium alginate | 0.5 |
| Lecithin | 0.5 |
| Sodium chloride | as desired |
| Buffer agent to adjust pH for desired stability | as desired |
| Water | to desired volume |

EXAMPLE 9

Tablets and capsules containing the ingredients indicated below may be prepared by conventional techniques and are useful in controlling fertility and controlling and regulating estrus in large domestic mammals in the manner described above given daily to said host.

| Ingredients | Weight (mg.) | | |
|---|---|---|---|
| | (a) Tablet | (b) Capsule | (c) Capsule |
| 9α-methyl 17α-propadienylestra-4en-17β-ol-3-one | 6 | 6 | 10 |
| Tragacanth | 10 | — | — |
| Lactose | 241.5 | 294 | 490 |
| Corn Starch | 25 | — | — |
| Talcum | 15 | — | — |
| Magnesium stearate | 2.5 | — | — |
| Total | 300.0 mg | 300 mg. | 500 mg. |

What is claimed is:

1. A compound of the formula

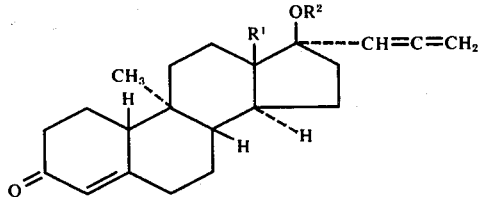

wherein
R$^1$ is alkyl having from 1 to 3 carbon atoms; and
R$^2$ is a hydrogen atom, methyl, acetoacetyl or alkanoyl having from 2 to 4 carbon atoms.

2. A compound of claim 1 wherein R$^2$ is a hydrogen atom.

3. A compound of claim 1 wherein R$^1$ is methyl.

4. The compound of claim 3 which is 9α-methyl-17α-propadienylestra-4-en-17β-ol-3-one.

5. A compound of the formula

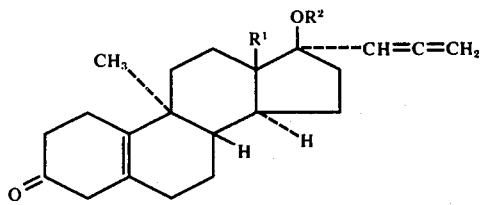

wherein
R$^1$ is alkyl having from 1 to 3 carbon atoms; and
R$^2$ is a hydrogen atom, methyl, acetoacetyl or alkanoyl having from 2 to 4 carbon atoms.

6. A compound of claim 5 wherein R$^2$ is a hydrogen atom.

7. A compound of claim 5 in which R$^1$ is methyl.

8. The compound of claim 7 which is 9α-methyl-17α-propadienylestra-5(10)-en-17β-ol-3-one.

9. A compound of the formula

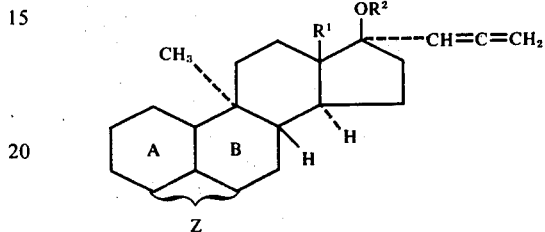

wherein
R$^1$ is alkyl having from 1 to 3 carbon atoms;
R$^2$ is a hydrogen atom, methyl, acetoacetyl or alkanoyl having from 2 to 4 carbon atoms; and
Z embracing rings A and B and the substituents thereon has structure

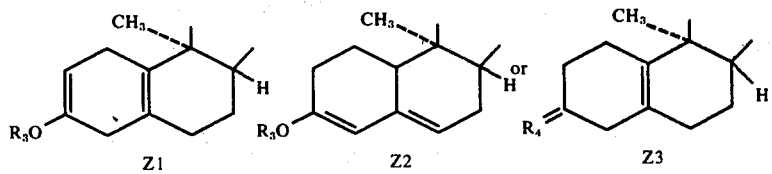

in which
R$^3$ is alkyl having from 1 to 4 carbon atoms, and
R$^4$ is (R$^{4'}$O)—$_2$ or

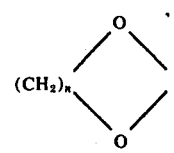

wherein
R$^{4'}$ is alkyl having from 1 to 4 carbon atoms, and
n is 2 or 3.

10. A compound of claim 9 wherein Z is Z1.

11. A compound of claim 10 wherein R$^1$ is methyl.

12. The compound of claim 11 which is 3-methoxy-9α-methyl-17α-propadienylestra-2,5(10)-dien-17β-ol.

13. A compound of claim 9 wherein R$^2$ is a hydrogen atom or methyl.

14. A compound of claim 13 wherein Z is Z1.

15. A compound of claim 14 wherein R$^1$ is methyl.

* * * * *